United States Patent
Ikeda

(10) Patent No.: US 7,402,249 B2
(45) Date of Patent: Jul. 22, 2008

(54) BLOOD PURIFICATION APPARATUS FOR ELEVATING PURIFICATION EFFICIENCY

(75) Inventor: Atsushi Ikeda, Yamagata-gun (JP)

(73) Assignee: JMS Co., Ltd., Hiroshima-shi (JP)

( * ) Notice: Subject to any disclaimer, the term of this patent is extended or adjusted under 35 U.S.C. 154(b) by 0 days.

(21) Appl. No.: 11/428,178

(22) Filed: Jun. 30, 2006

(65) Prior Publication Data

US 2007/0007209 A1    Jan. 11, 2007

Related U.S. Application Data

(63) Continuation-in-part of application No. 10/485,277, filed as application No. PCT/JP02/07777 on Jul. 31, 2002, now abandoned.

(30) Foreign Application Priority Data

Aug. 1, 2001    (JP)    ............... 2001-234141

(51) Int. Cl.
  *B01D 61/32*    (2006.01)
  *B01D 61/00*    (2006.01)

(52) U.S. Cl. ............ 210/647; 210/85; 210/86; 210/87; 210/90; 210/97; 210/143; 210/645; 210/646; 604/4.01; 604/5.01; 604/6.11; 604/28; 604/29

(58) Field of Classification Search ............ 210/85, 210/87, 90, 97, 143, 645, 646, 647, 739, 210/86; 604/4.01, 5.01, 6.11, 28, 29
See application file for complete search history.

(56) References Cited

U.S. PATENT DOCUMENTS

| 4,469,593 | A  | 9/1984 | Ishihara et al. |
| 4,722,798 | A  | 2/1988 | Goss |
| 4,832,839 | A  | 5/1989 | Tamura |
| 5,938,938 | A  | 8/1999 | Bosetto et al. |
| 6,689,083 | B1 | 2/2004 | Gelfand et al. |

FOREIGN PATENT DOCUMENTS

| JP | 57-78866 A    | 5/1982 |
| JP | 59-115051 A   | 7/1984 |
| JP | 5-115546 A    | 5/1993 |
| JP | 06-83723 B2   | 10/1994 |
| JP | 09-149935 A   | 6/1997 |
| JP | 11-221275 A   | 8/1999 |
| JP | 2001-540 A    | 1/2001 |
| WO | WO 00/25804 A2 | 5/2000 |

OTHER PUBLICATIONS

English translated Japanese Patent No. 11-221275.*

* cited by examiner

*Primary Examiner*—John Kim
(74) *Attorney, Agent, or Firm*—Westerman, Hattori, Daniels & Adrian, LLP.

(57) ABSTRACT

A blood purification method that purifies blood taken from a body by blood dialysis or by hemodiafiltration includes the step of changing an osmotic pressure of the blood to an increasing condition until a blood volume (BV level) attains a standard blood volume, in a former part of a blood purification process and the step of maintaining a standard blood volume and periodically changing the osmotic pressure of the blood in a later part of the blood purification process.

7 Claims, 2 Drawing Sheets

Dialysis Time

BLOOD PURIFICATION APPARATUS FOR ELEVATING PURIFICATION EFFICIENCY

This application is a continuation-in-part application of U.S. patent application No. 10/485,277, filed Apr. 12, 2004, abandoned, which is the national stage application filed under 35 U.S.C. § 371 of International Application No. PCT/JP02/07777, filed Jul. 31, 2002, which claims priority from Japan Application No. 2001-234141, filed Aug. 1, 2001. The entire contents of each of the aforementioned applications are incorporated herein by reference.

BACKGROUND OF THE INVENTION

1. Technical Field

The present invention relates to a blood purification method that can elevate blood purification efficiency, more concretely to a blood purification method that can control blood purification by confirming the patient's blood condition, and that can elevate purification efficiency such as water removal or removal of waste products, solutes and the like.

2. Background Art

For treating patients with impaired kidney function, blood purification such as hemodialysis or peritoneal dialysis and the like have been carried out conventionally. Hemodialysis is a treatment to purify blood by removing extra water or waste products and toxic agents in the blood, via a semipermeable membrane in form of hollow fiber. Thus, as for an apparatus that carries out hemodialysis, it is important to maintain adequately the patient's blood condition (blood volume circulating in the body) to carry out safe and effective hemodialysis. In case the target dialysis condition is an excessive setting for the patient, the blood circulating volume will decrease excessively and it may cause reduction of blood pressure or shock. On the contrary, if the dialysis condition is too gentle, there is a problem of hypertension or heart failure caused by insufficient water removal. Furthermore, naturally, it will be hard to improve symptoms of kidney failure according to insufficient dialysis.

Therefore, a hemodialysis apparatus performing water removal by monitoring a patient's blood condition have been proposed. For example, an apparatus that controls dialysis treatment by carrying out hemodialysis by measuring the Hematocrit level, and that gears and controls the blood pump, the water removal pump and the liquid supply pump, according to the blood circulating volume calculated from the Hematocrit level can be exemplified. The apparatus mentioned above has a simple construction so that anyone can use, but on the contrary, the adjustment of the dialysis time is difficult (extension of dialysis time is fatal), therefore, there was a problem that the control of the former part of the dialysis cannot be performed and that it is effective only to the reduction of blood pressure of the latter part.

In Japanese Laid-Open Patent Application No. 9-149935, a hemodialysis apparatus that controls the dialysis condition by monitoring the blood condition is disclosed. Moreover, in Japanese Laid-Open Patent Publication No. 6-83723, a controlling apparatus that estimates the body fluid condition with the Hematocrit level, and controls the blood pump or the ultra pressure according to said condition. However, as for the apparatus described above, there were problems that there were no safety mechanism to suppress the feedback control being out-of-control, or that the operator had to operate the-dialysis condition or the apparatus each time the blood condition departs from the defined condition.

Furthermore, the present inventors also have proposed in the past, a blood purification apparatus that can carry out hemodialysis treatment by monitoring the patient's blood condition. For example, the blood purification apparatus disclosed in Japanese Patent Application No. 10-101324 (Japanese Laid-Open Patent Application No. 11-221275) can be exemplified. However, as this apparatus gains the water removal volume in the former part of the dialysis, it has a merit of being able to control the blood circulating volume during dialysis within the predetermined range which can solve the problem of extension of dialysis time. But, on the contrary, it had demerits that it was necessary to define an alarm zone to control, that it was necessary to define controlling parameters in detail.

There were not only problems concerning the hemodialysis apparatus as described above, but also essential problems more important concerning the hemodialysis itself. These are problems of hemodialysis concerning dialysis efficiency such as solute removal, water removal and the like, which are disadvantages unavoidable for the hemodialysis membrane. In conventional hemodialysis, the removal of low-molecular-weight waste products was satisfactory, but as the removal efficiency of medium-molecular-weight was not good, it was provided to use a hollow fiber dialysis membrane with a larger diameter of the hole, to increase the removal efficiency of the medium-molecular-weight solutes. However, by using the dialysis membrane with a large diameter of the hole, the removal of medium-molecular-weight was improved but on the other hand, there were defects that albumin or other protein necessary for a living body were removed together

SUMMARY OF THE INVENTION

The object of the present invention is to solve the above-mentioned problems. That is, it is to provide a blood purification method that can carry out blood purification accurately and easily with a low risk to a patient, and moreover that can improve the dialysis efficiency.

To achieve the object, the present inventors have formed artificially an osmotic gradient (in other words, a difference of osmotic pressure) between the osmotic pressure of patient's blood and the osmotic pressure of water in the patient's cell and the intercellular substance during the blood purification, especially a repeating condition of increasing and decreasing to the blood osmotic pressure in the latter part of the blood purification, to improve efficiency of water removal or solute removal, that was made to be a basic technical philosophy. Thus, the present invention was completed according to this technical philosophy.

Further, the blood purification method of the present invention is a blood purification method which monitors blood index levels during blood purification, for example, the blood circulating volume or the change of blood circulating volume, etc. and controls the in vivo condition by controlling these blood index levels, and than can purify every cell throughout the body with a low risk to a patient, by generating an osmotic gradient, such as mentioned above, between the osmotic pressure of the patient's blood and that of water in the cells and the intercellular substances of the patient.

DESCRIPTION OF THE PREFERRED EMBODIMENTS

Figure 1:
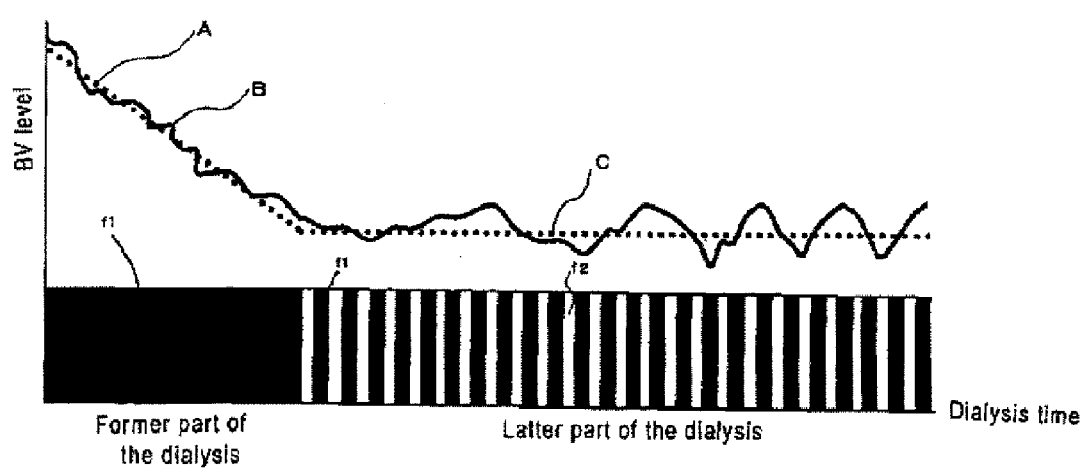
FIG. 1 is a diagram showing the former part of the blood purification process.

Originally, in the peripheral circulation system in vivo, material transfer is performed between the arteriola, the venula, the intercellular substances and the cells (Starling hypotesis), and according to this mechanism, the cells incorporate vital substances and excrete waste products. Further, large waste products are sent to the vein via the lymph duct to be removed.

As for the in vivo condition of the patient before blood purification, waste products are accumulated due to the impaired kidney function, thus the osmotic pressure of the blood, water in the intercellular substances and water in the cells are high, with excessive body fluid. The condition of excessive body fluid not only inhibits material transfer in both directions of the osmotic pressure of the patient's blood, and the water in the cell and the intercellular substance of the patient, but also degrades the lymph circulation. Thus, normal metabolism is not performed, and an inefficient condition will continue for a while after the initiation of dialysis. Therefore, it is important to set back rapidly the blood circulating volume to a normal blood circulating volume (herein after referred to as standard blood circulating volume), while it is dangerous to set to a standard blood circulating volume by ignoring the patient's blood vessel condition, for example, arteriosclerosis or circulation dynamics, and it is necessary to control the blood index levels in view of the blood vessel condition or circulation dynamics of the patient, when approaching the standard blood circulating volume. Thus, blood dialysis can be performed without affecting the peripheral blood circulation.

Therefore, in the blood purification method of the present invention, in the former part of the blood purification, it is intended to make rapidly a condition similar to that of the normal blood circulating volume, wherein the material transfer in both directions between the osmotic pressure of the patient's blood and water in the cell and the intercellular substance can be expected, to perform blood purification by changing the osmotic pressure of patient blood to the increasing condition. Then, in the latter part of the blood purification, the condition of normal blood circulating volume achieved by the former part of blood purification, that is a condition of blood volume wherein the peripheral circulation or blood pressure of the patient is maintained or cardiac overload is lowered is realized, the osmotic gradient between the osmotic pressure of the blood and that of the water in the cell and the intercellular substance is changed periodically to increase efficiency of water removal or solute removal. Further, the removal ability of specific solutes (particularly medium-molecular weight solutes, hard to transfer) can be improved, and every cell throughout the body can be purified, thus an excellent effect can be exerted.

For the reason that the efficacy of the blood purification as mentioned above can be reached, it is tentatively estimated that it is due to a phenomenon as follows.

When the blood with high osmotic pressure recycles in the body, the osmotic gradient between the blood and the water in the cell and the intercellular substance will become larger, the material transfer between the water in the cell and the intercellular substance and the blood will become larger and water will move from the cell and the intercellular substance to the blood side. At the same time, the components of the blood side will transfer to the cells. Then, the osmotic gradient of the blood and that of the water in the cell and the intercellular substance water will decrease gradually and it is assumed that the blood and the water in the cell and the intercellular substance would stabilize where the osmotic pressure is higher than usual. When the water in the cell and the intercellular substance which is stabilized where the osmotic pressure is high and the blood of lower osmotic pressure than usual will meet, the water will on the contrary flow in from the blood into the cell and the intercellular substance, and not only the transfer of water or small-molecule but transfer of medium or large molecular weight can be expected. Further, when the contact of the water in the cell and the intercellular substance which is stabilized where the osmotic pressure is high and the blood of the lower osmotic pressure than usual is repeated cyclically, according to the difference between the cycle and the transfer speed of each solute, it is expected the removal ability of specific material is improved.

As for a means that changes periodically the osmotic gradient between the osmotic pressure of the blood and the osmotic pressure of the water in the cell and the intercellular substance water osmotic pressure, for example, stopping the water removal or changing the blood purification conditions including the water removal speed, and using materials changing the osmotic pressure of the blood can be exemplified.

As for the material to be used to perform the operation of changing periodically the blood osmotic pressure to be high and low artificially as mentioned above, it has no specific limitation as long as it is a material that can achieve said object, and the osmotic pressure changing material such as electrolytes selected from sodium, calcium and magnesium, alkalizers selected from lactic acid and bicarbonic acid, and glucose, or a combination thereof and the like can be exemplified. Among these, the osmotic pressure changing material comprising sodium ion is preferable from the point of view of safety and effectiveness. As for the means for changing the osmotic pressure of the blood by using materials changing the osmotic pressure of the blood, for example, a means to inject the osmotic pressure changing materials to the dialysate in the dialysate circuit, for example a means for injecting sodium with an injector of fluid comprising sodium (hereinafter also referred to as sodium injector) can be exemplified.

In case of injecting fluid comprising sodium as an osmotic pressure changing material into the dialysate, it is preferable that the concentration is of a high content, for example 145-150 mEq/l to increase blood osmotic pressure, and that the concentration is of a low content, for example 140-143 mEq/l to lower the blood osmotic pressure.

As for the blood purification method, the method of hemodialysis, hemofiltration (HF) and hemodiafiltration (HDF) can be exemplified, and among these, HF or HDF supplying dialysate by on-line is preferable.

In the following, the blood indication levels such as the BV level used for the control in the blood purification method of the present invention will be explained.

(1) The BV Level

The BV level is the abbreviation for the Blood Volume level and is the index of the circulating blood volume which is the indication level to check the condition of the circulating blood volume of each patient.

(2) The Standard Blood Volume

As for the blood volume to be maintained during dialysis, the blood volume maintained normally by the patient is believed to be the standard blood volume. The standard blood volume is a blood volume which the patient would have if healthy, by considering factors that might influence the human blood volume, for example the patient's age, sex, body height and the like, defined beforehand by doctors and the like.

3. ΔBV

It refers to the BV volume change, and it can be calculated by the following formula: ΔBV [BV volume change]=(Ht at the time of the initiation of the dialysis/Ht at the time of the measurement)−1 The Ht is the abbreviation of Hematocrit showing the bulk ratio of red corpuscle in the whole blood.

4. ΔBV %

It is the ratio of the BV volume change, and as shown in the following formula, the ΔBV level at the time of the measurement is divided by $BV_0$ and is expressed in percentage. ΔBV %=ΔBV/$BV_0$×100.

5. BV %

It is calculated by dividing the BV level at the time of the measurement by $BV_0$ and is expressed in percentage. BV %=BV level at the time of the measurement/$BV_0$×100

If the standard blood volume is defined, the target BV % at a given time point of blood purification can be calculated from the defined standard blood volume and $BV_0$. Target BV %=standard blood volume/primary blood volume×100

$BV_0$ which is the primary blood level, can be calculated by a common method, for example according to the Hematocrit level.

According to the embodiment of the present invention, a blood purification apparatus having excellent effects as follows can be obtained.

(1) The blood purification can be carried out accurately by an easy operation.
(2) The blood purification can be carried out safely and physiologically for a living body.
(3) The dialysis efficiency can be improved (elevated), and as a result the extension of the blood purification time can be avoided and the removal amount of medium-molecular-weight waste products is increased.

FIG. 1 is a figure explaining that in the former part of the blood purification process. The purification process is performed by maintaining the blood osmotic pressure continuously in an increasing condition with the use of a sodium rich dialysate, and according to the target control line A which is constituted with the target BV level defined at plural time points chronologically during blood purification process, and that in the latter part of the purification process the purification process is performed by injecting sodium rich dialysate and normal dialysate into the blood circuit or into the circuit supplying dialysate periodically to form periodically a repeating condition of increasing and decreasing the blood osmotic pressure artificially, and by maintaining the standard blood volume according to the target control line C which is the standard blood volume. Line B is the actual measured BV line constituted with the BV level, actually measured. The Y axis shows the BV level, and the X axis show the blood purification time. Further, f1 represents the use of the sodium rich dialysate and f2 represents the use of the normal sodium dialysate.

Figure 2:
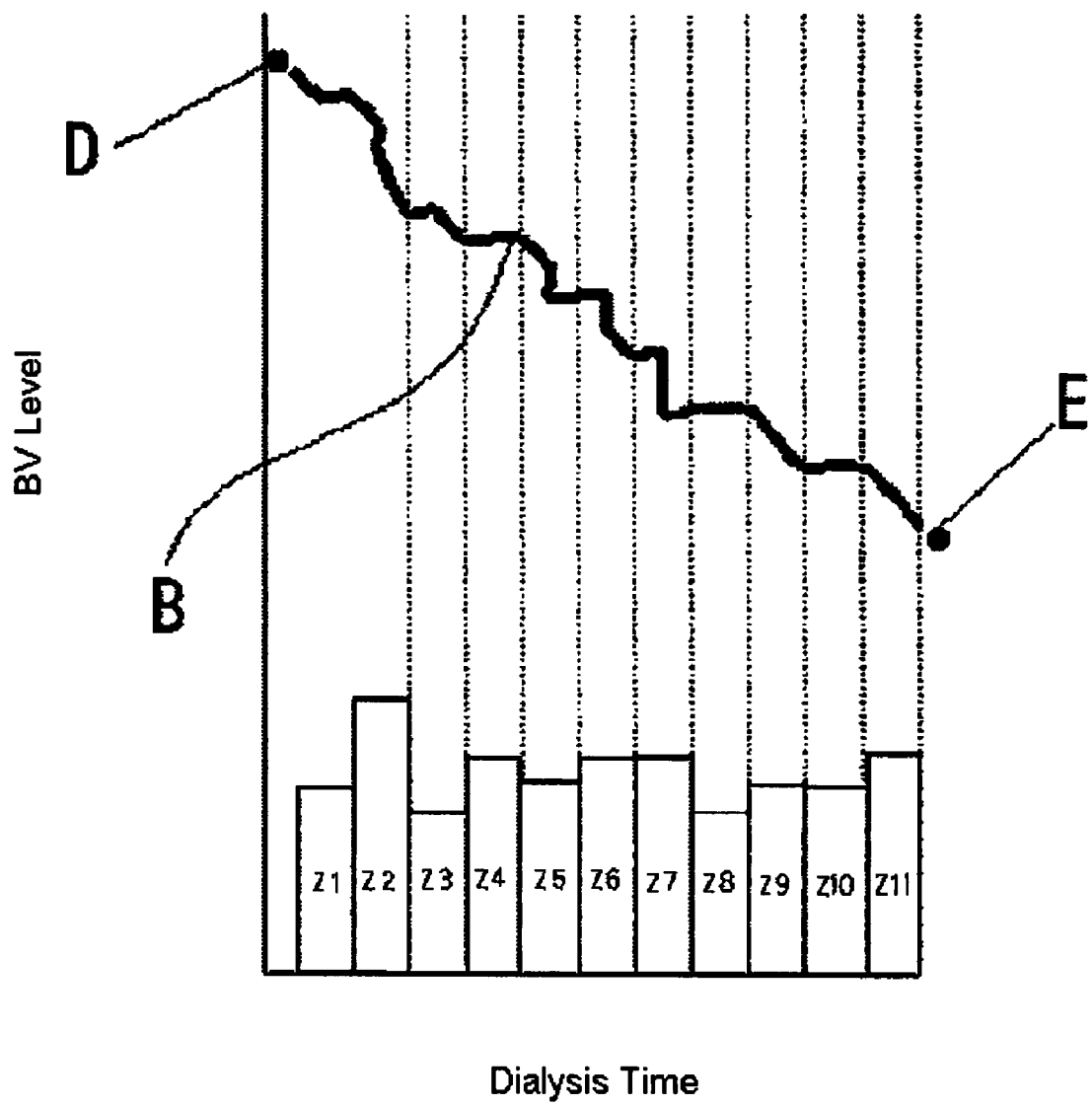
FIG. 2 is a diagram showing the BV level change from the primary blood volume to the standard blood volume

FIG. 2 is a figure showing the BV level change from the primary blood volume until it reaches the standard blood volume, and the relation with the actual water removal volume. In FIG. 2, D represents $BV_0$ (primary blood volume); Line B, the actual measured BV line; E, the standard blood volume; Y axis, the BV level; and X axis, the blood purification time. Further, Z1-Z11 represent the actual water removal volume (ml), chronologically.

The present example is an example of improving the dialysis efficiency by combining sodium infuser and on-line HDF, and is explained according to FIGS. 1 and 2.

In the blood purification apparatus of the present example, Na infuser and on-line HDF is combined, and also by using a UFR controller, the compressing volume from the dialysate and the water removal volume from the dialyzer are made to be the same amount, that is to be balanced. Therefore, the blood osmotic pressure can be changed rapidly, sharply, and also in a wide range. Furthermore, to change the electrolyte of the dialysate circulating in the dialysate circuit, the sodium injector that injects solution comprising rich sodium into the dialysis circuit is suitable.

The sodium injector is disposed on the upper stream side of the hemodialyzer of the dialysate circuit, and is able to circulate solution comprising rich sodium. In the primary dialysis, by using an Na injector, the blood where the rich Na dialysate is injected becomes hyperosmotic, and the water removal speed will be high and it will be possible to elevate the material removal ability from the blood. The water removal is performed by targeting the BV volume of the target control line A, and the circulating blood volume is set from the primary blood level to the standard blood volume E.

Next, when the latter part of the dialysis is started, the Na injector is operated intermittently and a rich Na dialysate and a normal dialysate are produced alternatively. By performing on-line HDF with the dialysate, the osmotic gradient between the cell and the intercellular substance and the blood is formed periodically and the intended effect was achieved. Meanwhile, in the present example, control of blood purification was performed by using the BV level, while control of the blood purification can be performed by using the blood index levels other than the BV level.

The invention claimed is:

1. A blood purification method that purifies blood taken from a body by blood dialysis or by hemodiafiltration, comprising:
    purifying blood maintaining an osmotic pressure of the blood at an increased level until a blood volume (BV level) attains a preset patient's standard blood volume, in a former part of a blood purification process; and
    maintaining the preset patient's standard blood volume and periodically changing the osmotic pressure of the blood by injecting alternately a high-concentration electrolyte liquid sufficient to increase the osmotic pressure of the blood and a low-concentration electrolyte liquid sufficient to decrease the osmotic pressure of the blood in a latter part of the blood purification process.

2. The blood purification method according to claim 1, wherein the blood purification method is an on-line hemodiafiltration method.

3. The blood purification method according to claim 1, further comprising controlling the blood purification by a target control line constituted with blood index levels set at plural time points chronologically.

4. The blood purification method according to claim 3, wherein in the former part of blood purification process, the target control line is constituted with target blood volume.

5. The blood purification method according to claim 3, wherein in the latter part of blood purification process, the target control line is constituted with the patient's standard blood volume.

6. The blood purification method according to claim 1, the high-concentration electrolyte liquid is of the content of sodium ion of 145-150 mEq/l and the low-concentration electrolyte liquid is of the content of sodium ion of 140-143 mEq/l.

7. A blood purification method according to claim 1, further comprising controlling a material transfer between a cell and intercellular substance and the blood.

* * * * *